United States Patent [19]

Pranger

[11] Patent Number: 5,128,323
[45] Date of Patent: Jul. 7, 1992

[54] COMPOSITION HAVING ANTI-ENDOTOXIC ACTIVITY

[75] Inventor: Maarten H. Pranger, Weesp, Netherlands

[73] Assignee: Duphar International Research B.V., Weesp, Netherlands

[21] Appl. No.: 355,505

[22] Filed: May 23, 1989

[30] Foreign Application Priority Data

May 26, 1988 [NL] Netherlands ............... 8801349

[51] Int. Cl.$^5$ ............... A61K 31/70; C07H 1/06; C13K 5/00
[52] U.S. Cl. ............... 514/23; 514/53; 536/1.1; 536/125; 536/127; 127/46.2; 127/53
[58] Field of Search ............... 514/23, 53; 536/1.1, 536/125, 127; 127/46.2, 53

[56] References Cited

U.S. PATENT DOCUMENTS

| | | | |
|---|---|---|---|
| 2,524,414 | 10/1950 | Wolfrom et al. | 536/127 |
| 3,816,174 | 6/1974 | Nagasawa et al. | 536/127 |
| 4,067,748 | 1/1978 | Rowe | 127/36 |
| 4,536,221 | 8/1985 | Carobbi et al. | 536/127 |
| 4,555,271 | 11/1985 | Carobbi et al. | 536/127 |
| 4,565,582 | 1/1986 | Filippini et al. | 536/127 |
| 4,931,554 | 6/1990 | Bijl et al. | 536/124 |
| 4,957,564 | 9/1990 | Carobbi et al. | 536/127 |
| 5,003,061 | 3/1991 | Carobbi et al. | 536/127 |

FOREIGN PATENT DOCUMENTS 0322499 7/1989 European Pat. Off. .

OTHER PUBLICATIONS

Van Vugt et al; Chemical Abstracts 99:17787d (1983).
Liehr et al; Hepato.-Gastroenterology 27:356-360 (1980).
Van Vugt et al; Hepatology 3(2):236-240 (1983).
de Groot et al; Hepato-Gastroenterology 30:240-242 (1983).
Ditter et al; Gastroenterology 84:1547-1552 (1983).
Lind et al; Anesthesiology 61:544-550 (1984).

*Primary Examiner*—Johnnie R. Brown
*Assistant Examiner*—Nancy S. Carson
*Attorney, Agent, or Firm*—Stevens, Davis, Miller & Mosher

[57] ABSTRACT

The invention relates to pharmaceutical compositions having antiendotoxic activity, comprising as the active component a fraction which can be isolated from lactulase syrup by means of absorption at a sulphonated polystyrene cation resin in the $Ca^{2+}$- form and elution with a suitable solvent. The lactulose syrup can be obtained by basic isomerization of lactose at elevated temperature, optionally in the presence of sodiumsulphite.

2 Claims, No Drawings

COMPOSITION HAVING ANTI-ENDOTOXIC ACTIVITY

The invention relates to a compound or a mixture of compounds having an anti-endotoxic activity.

In the period from 1979 to 1980, several investigators described that lactulose was to have a favorable influence on the phenomena which are associated with endotoxaemia.

These endotoxic phenomena are caused directly and/or indirectly by endotoxins in the circulation which originate from the cell wall of dead bacteria. It is assumed that endotoxins via the induction of tumor necrosis factor (TNF) by the macrophage start a mechanism by which various syndromes may occur, for example,

- tubulus necrosis in the kidneys followed by renal insufficiency (hepto-renal syndrome)
- damage of leucocytes and fever
- enhanced vessel permeability resulting in maldistribution of the circulating volume and malperfusion of organs (endotoxic shock), which results in deficiency of various organs
- damage of thrombocytes resulting in clotting disorders
- liver damage resulting in hyperglycaemia.

A sever endotoxaemia ultimately causes severe metabolic and respiratory disorders, which results in shock followed by death.

That endotoxins attain the blood may be caused by:
- an infection with gram-negative micro-organisms (i.e. sepsis), for example, in infectious diseases, during and after surgery and traumata
- an enhanced absorption of endotoxins originating from the intestinal flora to the portal circulation, for example, in gastrointestinal diseases like M. Crohn, ulcerative colitis, peritonitis, and paralytic ileus
- a deficient detoxicating function of the liver in liver and biliary duct diseases as in the case of hepatitis, liver cirrhosis, P.S.E. and obstructive jaundice.

As stated hereinbefore several investigators have described that lactulose was to have anti-endotoxin activity.

Lactulose is prepared by basic isomerization of lactose at a high temperature whether or not in the presence of sodium sulphite.

After thorough research it has now been found that the anti-endotoxic activity as it has been described for lactulose syrup cannot be ascribed to lactulose itself but to a fraction which is present in the lactulose syrup and which can be isolated from the lactulose syrup by means of absorption on a sulphonated polystyrene cation resin in the $Ca^{2+}$ form by elution with a suitable eluent, for example, water. It has now been found that substantially the whole desired anti-endotoxic activity is present in the said fraction.

The invention therefore relates to pharmaceutical compositions having anti-endotoxic activity which comprise the above-mentioned fraction in a form suitable for administration as an active component.

The compositions according to the invention may be used orally, parenterally or topically for treating and/or preventing the negative effects provoked by endotoxins in general, in particular endotoxaemia.

The anti-endotoxic activity was determined by means of the following test models:

I. LIMULUS AMOEBOCYTE LYSATE TEST (LAL-TEST)

As substances to be tested were used lactulose syrup as it is marketed by Duphar under the name of Duphalac (A), and the fraction to which the invention relates (B) which after absorption is eluted from a column in the $Ca^{2+}$-form.

Of the substances A and B to be tested 0.9 ml of a 5% solution diluted with pyrogen-free water were added to 0.1 ml of endotoxin (E. coli 0111 B4 of Difco, U.S.A.) and incubated for two hours at 37° C. in bottles of polypropylene. 50 µl of the Limulus amoebocyte lysate (Sigma, U.S.A., E-toxate batch 85F-0138) were pipetted into the wells of a U-shaped microtiter plate (Sterilin, Great Britain). 50 µl of the incubated mixture of endotoxin and substance to be tested were added and the microtiter plate was covered with a plastic lid. After incubating at 37° C. for one hour it was determined whether gelation occurred by the addition of 50 µl of a 0.05% solution of crystal violet in water. The plates were inspected at an angle of incidence of 30°–40°. Gelation was evaluated positive when the dye did not mix with the contents of a well and did not color same.

The results obtained are recorded in the table hereinafter:

TABLE

| Endotoxin conc. | Examined substance | |
| --- | --- | --- |
| | A | B |
| 1 ng/ml | + | + |
| 500 pg/ml | + | + |
| 250 pg/ml | + | −/+ |
| 100 pg/ml | + | − |
| 50 pg/ml | + | − |
| 25 pg/ml | +/− | − |
| 12.5 pg/ml | − | − |

In accordance with accepted terminology in this art, the meanings of the symbols are as follows: "+": active in the LAL test "+/−": slightly active in the LAL test "−/+": questionable activity in the LAL test "−": no activity in the LAL test.

It appears from these results that the anti-endotoxic activity of B, i.e. the fraction to which the invention relates, is at least ten times as large as that of lactulose syrup (A).

II. MONOCYTE/TNF-TEST

Tumor Necrosis Factor (TNF) is reported to be one of the main mediators of endotoxin toxicity. TNF is released by macrophages in vivo in response to endotoxin stimulation.

The in vivo situation can be imitated in an in vitro model: monocytes, the macrophage precursor cells in blood, are isolated from donor blood (J. Immunol. (1987), 139, 3536–3541) and incubated in a suitable medium (for example RPMI 1640 supplemented with 10% bovine calf serum and optionally antibiotics) to keep them metabolically active. Addition of endotoxin to the incubation medium (0.3 ng/ml) leads to the production and release of TNF. TNF can be measured in the supernatant fluid using the ELISA-technique.

The fraction according to the invention has been tested in this monocyte/TNF system to measure the antiendotoxic activity, i.e. the inhibition of endotoxin-induced TNF production. The results are presented in the following table:

| component | conc. w/v % | % inhibition of TNF production |
|---|---|---|
| lactulose syrup | 0.8 | >90 |
| fraction | 0.06 | >90 |
| lactulose | 0.01 | 4 |
| lactose | 0.01 | 2 |
| galactose | 0.01 | 5 |
| buffer | — | 0 |

What is claimed is:

1. A substantially lactulose-free pharmaceutical composition having anti-endotoxic activity, containing as an active component the fraction which is isolated from lactose syrup by means of adsorption in a sulphonated polystyrene cation resin in the $Ca^{2+}$ form and subsequent elution from said resin with a suitable solvent.

2. A substantially lactulose free composition of matter which is a fraction isolated from lactulose syrup produced by basic isomerization of lactose in solution, and optionally in the presence of sodium sulphite, through adsorption on a sulphonated polystyrene cation resin in the $Ca^{2+}$-form, and elution with an eluent.

* * * * *